United States Patent [19]
Ells et al.

[11] Patent Number: 5,616,340
[45] Date of Patent: *Apr. 1, 1997

[54] PROCESS FOR MAKING A HARD-CANDY BASED ORAL PHARMACEUTICAL LOZENGE CONTAINING AN ANTACID

[75] Inventors: Thomas S. Ells, Ft. Washington; Joseph R. Luber, Quakertown, both of Pa.

[73] Assignee: McNeill-PPC, Inc., Fort Washington, Pa.

[*] Notice: The term of this patent shall not extend beyond the expiration date of Pat. No. 5,399,354.

[21] Appl. No.: 349,035

[22] Filed: Dec. 2, 1994

Related U.S. Application Data

[62] Division of Ser. No. 69,133, May 28, 1993, Pat. No. 5,399,354.

[51] Int. Cl.$^6$ ............................................. A61K 9/20
[52] U.S. Cl. ...................... 424/440; 424/485; 424/488
[58] Field of Search ............................ 424/440, 441, 424/464, 485

[56] References Cited

U.S. PATENT DOCUMENTS

| | | | |
|---|---|---|---|
| 4,127,650 | 11/1978 | Buehler | 514/63 |
| 4,163,777 | 8/1979 | Mitra | 424/468 |
| 4,230,693 | 10/1980 | Izzo | 424/683 |
| 4,288,439 | 9/1981 | Crossley | 514/335 |
| 4,316,888 | 2/1982 | Nelson | 424/602 |
| 4,372,942 | 2/1983 | Cimiluca | 424/440 |
| 4,396,604 | 8/1983 | Mitra | 424/602 |
| 4,425,332 | 1/1984 | James | 423/89 |
| 4,910,023 | 3/1990 | Botzolakis | 424/470 |
| 5,047,248 | 9/1991 | Calanchi | 424/485 |
| 5,095,035 | 3/1992 | Eby | 514/494 |
| 5,156,845 | 10/1992 | Grodberg | 424/440 |
| 5,178,850 | 2/1993 | DuRoss | 424/48 |

FOREIGN PATENT DOCUMENTS

| | | |
|---|---|---|
| 1111766 | 11/1981 | Canada. |
| 0166440 | 1/1986 | European Pat. Off.. |

Primary Examiner—Thurman K. Page
Assistant Examiner—William E. Benston, Jr.
Attorney, Agent, or Firm—Connolly & Hutz

[57] ABSTRACT

A hard-candy based lozenge containing an antacid is produced in a manner compatible with a continuous process method of manufacture. Sucrose solution, corn syrup, and a carbonate antacid are mixed, the mixture is heated, the mixture is further heated and exposed to a vacuum. The mixture is then mixed with cold-flow enhancers, flavorings, and colorings, and finally tempered and formed into lozenges of exceptional efficacy and taste. The lozenges thus formed contain 600 mg of calcium carbonate or magnesium carbonate.

17 Claims, 1 Drawing Sheet

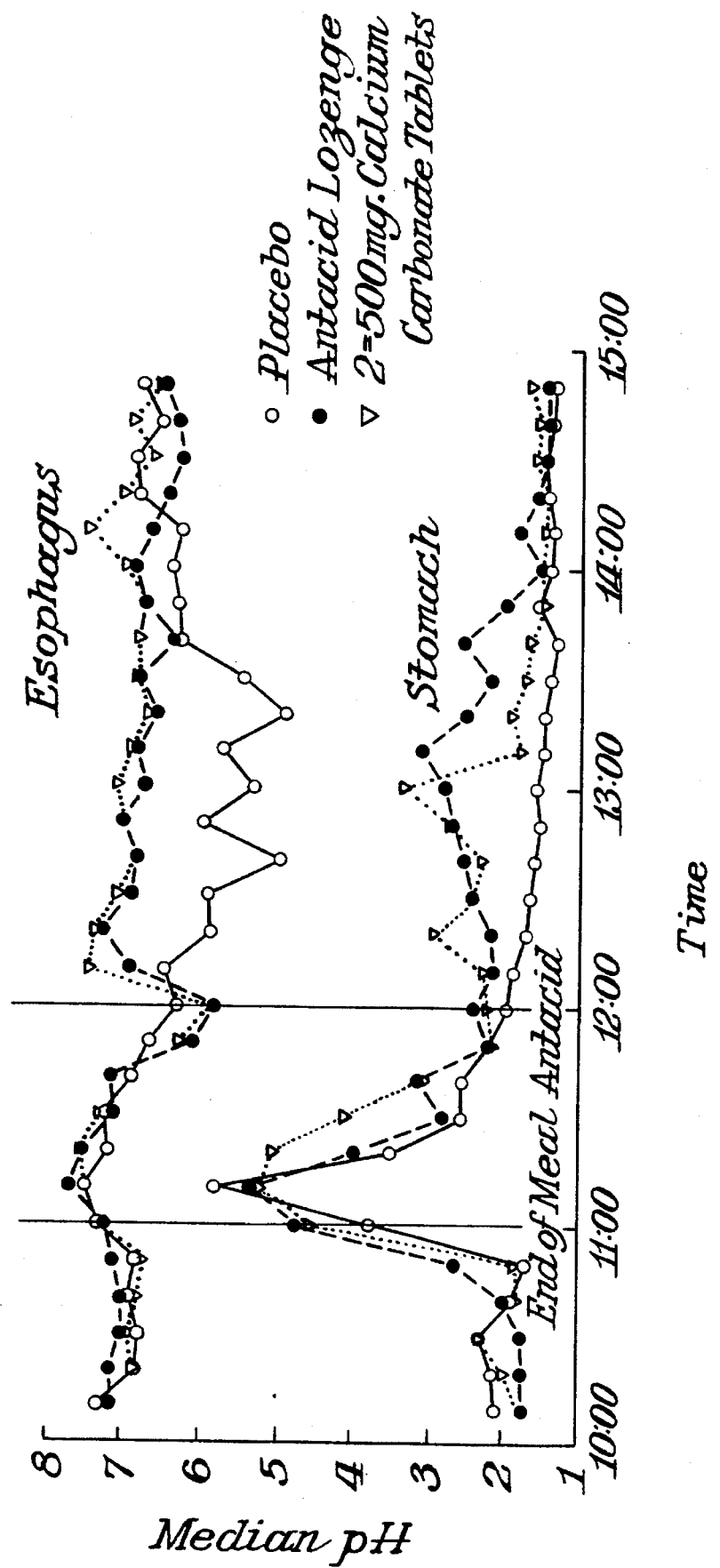

PROCESS FOR MAKING A HARD-CANDY BASED ORAL PHARMACEUTICAL LOZENGE CONTAINING AN ANTACID

This application is a continuation application from our earlier application, Ser. No. 08/069,133, filed May 28, 1993, now U.S. Pat. No. 5,399,354.

BACKGROUND OF THE INVENTION

1. Field of the Invention

The present invention relates to a method of making a hard-candy based pharmaceutical lozenge which continuously and efficiently dispenses an antacid preparation in a highly palatable manner, and a lozenge made by such a process.

2. Description of the Prior Art

A wide variety of conditions, such as stress, poor dietary habits, and chemical or drug stimulation, can result in the overproduction and accumulation of acidic substances in the gastrointestinal tract. These acidic substances can concentrate particularly in the stomach and esophagus causing physical discomfort, often serious. This condition may pose long-term deleterious physiological effects such as the onset of ulcerous conditions. An excellent summary of the effects of acid on the gastrointestinal tract is provided by W. Ganet, "Antacid Products", *Handbook of Nonprescription Drugs,* Sixth Edition, 1982, Chapter 3, pages 19–27.

Various treatment means may be undertaken by those afflicted with gastric discomfort. Among them are exercise, stress-reduction techniques, behavior modification, and pharmaceutical therapy.

Each of these treatment regimens has a similar disadvantage—a lack of positive incentive to continuously undergo therapy. Exercise requires physical exertion, stress-reduction techniques such as massage, counseling, and sedative drug therapy are expensive, time-consuming, and often invasive. Behavior modification is unpredictable, and prescription pharmaceutical preparations are expensive. Nonprescription remedies may also be expensive to manufacture on a large scale or, more importantly, carry the medicament stigma of a foul or unpleasant taste, texture or feel.

Prior art antacids, one of the most popular being marketed under the familiar trademarks of MYLANTA®, are available for oral pharmaceutical treatment of ailments resulting from excess stomach acid. However, common complaints arising from these products are the gritty or chalky taste from the antacid portion of the medicament, leading to less continuous use (noncompliance) and consequently less effective treatment.

Various solutions have been proposed for this taste-texture problem's solution. Some of these solutions are as follows:

U.S. Pat. No. 4,425,332, issued on Jan. 10, 1984 to James, and is incorporated herein by reference. James discloses that oral antacid compositions usually have the salts, hydroxides, or carbonates of aluminum, calcium, or magnesium as active antacid ingredients.

To overcome the gritty and chalky taste/feel of the antacid, James discloses finely dividing the solid antacid and combining it with a flavored base, in the form of a fondant ("creamy") confectionery, in the texture of a candy bar or soft sweet. The antacid may also be incorporated in an edible coating, or in a cake-like mixture.

U.S. Pat. No. 4,910,023, issued on Mar. 20, 1990 to Botzolakis et al., is incorporated by reference. Botzolakis discloses the masking of hygroscopic malflavored drugs by a wet granulation process followed by drying which coats the drug particles with silicon dioxide to mask unpleasant tastes.

U.S. Pat. No. 4,396,604, issued on Aug. 2, 1983 to Mitra, and is incorporated herein by reference. Mitra discloses a simethicone antacid lozenge, and a batch method of combining simethicone, an antiflatulent, with an antacid, in a lozenge of hard candy in a manner by which the simethicone retains its antiflatulent properties. The Mitra simethicone lozenge, as disclosed, describes the composition as containing from 55–90% of sucrose solids and 10–45% of corn syrup with the simethicone; noncariogenic candy compositions with the simethicone; and candy compositions containing sugar alcohols with the simethicone.

U.S. Pat. No. 4,163,777 issued Aug. 7, 1979, also to Mitra. Mitra '777 discloses an antacid-containing matrix formed by compression which is said to be slowly-dissolving, and a method of treating patients using the slowly-dissolving lozenge composition. The lozenge is formed from a matrix including a sugar or sugar alcohol; a gel-forming swelling agent; and a water-insoluble lipid material.

While these prior art disclosures may be effective in theory, none has disclosed or contemplated this method of making a lozenge containing antacid which is inexpensive, has exceptional efficacy, and has a taste pleasing enough to provide the desired positive reinforcement to encourage compliance with an effective treatment regimen. The applicants have invented a novel method of manufacturing lozenges which have excellent taste properties, and are simple and cost effective to manufacture.

SUMMARY OF THE INVENTION

To overcome the problems associated with the large-scale manufacture of pleasant-tasting lozenges suitable for treatment of acidic conditions of the gastrointestinal tract, this invention contemplates a continuous-process method of forming hard-candy based antacid lozenges, and the antacid-containing hard-candy lozenges formed by this process. The method comprises mixing about 50–55% by weight of sucrose solution with about 45–50% by weight of corn syrup to form a hard-candy lozenge base, adding an antacid, cooking the mixture in a precooker, cooking the resulting molten antacid-containing candy mass in a cooker, vacuum treating the molten candy mass, continuously mixing in flavorings, colorings, and glycerine or propylene glycol to sustain cold flow of the mass, forming the mass into a continuous band, and forming the lozenges from the band, all in a continuous, cost effective, simple process.

The antacid lozenges thus formed have a content of from 38.5–46.5% sucrose, 31.5%–38.5% corn syrup, 15–30% antacid, 1.5–1.6% cold flow enhancer, and 0.2–4% concentrated flavorings.

DESCRIPTION OF THE DRAWING

FIG. 1 is a graph showing gastric pH and esophogeal pH plotted against time.

DETAILED DESCRIPTION OF THE INVENTION

The present invention involves the large scale production, in a continuous process, of medicaments in a hard-candy base. The starting materials are calcium or magnesium carbonate in a powdered form, a solution of sucrose in water at about 65–70% concentration, and a solution of corn syrup at about 78–82% concentration.

In the process of the present invention, calcium carbonate is slurried into sucrose solution in a continuous fashion in a large-capacity stainless steel mixing tank and corn syrup may optionally be added at this step in the process. Under agitated mixing, the combination of ingredients is made homogeneous. The finished mixture is then pumped via a positive-displacement pump to a holding tank containing enough liquid to maintain the continuous process. The mixture is then pumped by a second positive-displacement pump through a precooker, where the temperature of the mixture is raised to about 110° C. for about 5–10 minutes as the mixture passes through the precooker. The corn syrup then, in a preferred embodiment of the invention, may be added to this precooked mixture to reduce energy consumption during the process.

After exiting the precooker, the molten mass is pumped by another pump through the cooker, where the temperature of the molten mass is raised to about 140°–155° C. for about 1 minute or longer to cause moderate sugar inversion. A vacuum tank then draws the molten candy mass into a chamber where a vacuum is applied, reducing the moisture content to approximately 0.5–4%. The candy mass emerges from the vacuum as a continuous ribbon of heavily viscous fluid, and is drawn by rollers from the vacuum chamber into an in-line mixer, where about 1.0–2.0% propylene glycol or 0.5–1.5% glycerine to enhance the cold-flow properties of the mixture, about 0.10–3.0% flavoring, and optionally about 0.10–0.20% coloring is added.

The final mixture passes through the in-line mixer onto a tempering band, is formed into a rope, and compressed into lozenges weighing generally between 2 and 3 grams.

The lozenge formed by this process, by weight, is about 15–30% by weight antacid, about 38.5–46.5% by weight sucrose, about 31.5%–38.5% by weight corn syrup, about 0.20–4% concentrated flavorings and colorants, and up to 2.0% propylene glycol, glycerine, or a mixture of glycerine and propylene glycol.

The process is best described by reference to the following examples.

Example 1

352.7 kg of liquid sucrose at 67% solid concentration were charged into a 120 gallon stainless steel mixing vessel. 185.07 kg of calcium carbonate were added while stirring. After the mixing was complete, an additional 110.41 kg of liquid sucrose were added and the contents of the stainless steel mixture were mixed to homogeneous consistency.

The calcium carbonate/sucrose slurry was pumped by a positive displacement pump into a pre-cooker, where it was heated to 110° C. Simultaneously, 80% solid Concentrate corn syrup was pumped into the pre-cooker at a rate such that the mixture was 45 parts corn syrup to 55 parts sucrose by dry weight.

This liquid composition was pumped into a cooker operating at a temperature of 145° C., and drawn into a chamber under a vacuum for about 1–2 minutes.

The cooked mass is continuously drawn by rollers from the vacuum chamber into an in-line mixer for mixing. While in the mixer, 1.58% propylene glycol, 0.14% flavoring, and 0.14% coloring were added continuously to color the cooked mass.

The mixture passed to a tempering band, was formed into a rope, and compressed into lozenges. Thereafter, the lozenges were cooled in a cooling tunnel.

The lozenges formed by this process were found to weigh 2.56 grams and contain 600 mg of calcium carbonate. Testing revealed the lozenge to have an actual acid neutralizing capacity of about 11.6 mEq and remained stable under accelerated storage conditions.

Example 2

The procedure of Example 1 was followed, with the exception that the second cooking temperature was 150° C.

Experimental Testing

Lozenges according to the present invention containing 600 milligrams of calcium carbonate were compared to two calcium carbonate tablets containing 500 mg each for the effect of esophageal and gastric pH. Six volunteer patients suffering from acid indigestion and heartburn were intubated with antimony pH probes positioned in the stomach and the esophagus. After consuming an acid-inducing meal, the patients were given one of the antacid lozenges according to the present invention, and pH was measured over time. The experiment was repeated, using 2 calcium carbonate tablets of 500 mg calcium carbonate each, and taking pH readings over time. Finally, the experiment was conducted with a placebo, taking pH readings over time. The results indicated that 1 lozenge raised the pH in the esophagus and stomach in an amount equivalent to 2 500 milligram calcium carbonate tablets. See FIG. 1. In the Esophagus, total time at low pH was less for the lozenge than for the 2 calcium carbonate tablets, indicating superior effectiveness. Taste testing confirmed that the lozenge was extremely palatable.

We claim:

1. A hard-candy lozenge containing an antacid, which is manufactured by a process which comprises mixing liquid sucrose, corn syrup, and a carbonate antacid into a mixture, heating the mixture to a first temperature by a cooking means, transferring the mixture to a second cooking chamber and heating the mixture to a second temperature, exposing said mixture to a vacuum, transferring the mixture to an in-line mixer, mixing the mixture in the in-line mixer and adding a cold-flow enhancer, favoring, and optionally coloring, and forming the mixture into lozenges.

2. The lozenge prepared by the process of claim 1, wherein the ratio of sucrose to corn syrup is within the range of 1.22:1 to 1:1.

3. The lozenge prepared by the process of claim 1, wherein the ratio of sucrose solids to corn syrup solids is 11:9.

4. The lozenge prepared by the process of claim 1, wherein the first temperature has a range of 105°–115° C.

5. The lozenge prepared by the process of claim 1, wherein the first temperature has a range of 108°–112° C.

6. The lozenge prepared by the process of claim 1, wherein the first temperature is about 110° C.

7. The lozenge prepared by the process of claim 1, wherein the second temperature has a range of 140°–155° C.

8. The lozenge prepared by the process of claim 1, wherein the second temperature has a range of 143°–147° C.

9. The lozenge prepared by the process of claim 1, wherein the second temperature is about 145° C.

10. The lozenge prepared by the process of claim 1, wherein the carbonate antacid is magnesium carbonate.

11. The lozenge prepared by the process of claim 1, wherein the carbonate antacid is calcium carbonate.

12. The lozenge prepared by the process of claim 1, wherein the carbonate antacid introduced is 15–30% by weight of the lozenge.

13. The lozenge prepared by the process of claim 1, wherein the cold-flow enhancer is glycerine.

14. The lozenge prepared by the process of claim 1, wherein the cold-flow enhancer is propylene glycol.

15. The lozenge prepared by the process of claim 1, wherein the cold-flow enhancer is introduced in an amount from 0.5–2.0% by weight.

16. The lozenge prepared by the process of claim 1, wherein the corn syrup is introduced continuously while heating the mixture to the first temperature.

17. A hard-candy lozenge containing an antacid, which is prepared by a process which consists essentially of mixing 67% concentrated aqueous liquid sucrose, 80% concentrated aqueous corn syrup, and calcium carbonate into a mixture, heating the mixture to about 110° C. by a cooking means, transferring the mixture to a vacuum-cooking chamber and heating the mixture in the vacuum-cooking chamber to about 145° C. under a negative pressure vacuum of 0.8 to 1.2 bar, transferring the mixture to an in-line mixer, mixing the mixture in the in-line mixer and adding about 1.5% propylene glycol or glycerine, 0.14% flavoring, and 0.14% coloring, and forming the mixture into lozenges.

\* \* \* \* \*